United States Patent [19]

Bamberg et al.

[11] 4,203,972
[45] May 20, 1980

[54] PENICILLIN COMPOSITION

[75] Inventors: Peter Bamberg, Zürich, Switzerland; Bertil Å. Ekström, Södertälje, Sweden; Ulf E. Forsgren, Gävle, Sweden; Berndt O. H. Sjöberg, Södertälje, Sweden

[73] Assignee: Astra Pharmaceutical Products, Inc., Framingham, Mass.

[21] Appl. No.: 889,410

[22] Filed: Mar. 23, 1978

Related U.S. Application Data

[63] Continuation-in-part of Ser. No. 464,157, Apr. 25, 1974, which is a continuation-in-part of Ser. No. 302,423, Oct. 31, 1972, abandoned.

[30] Foreign Application Priority Data

Nov. 1, 1971 [GB] United Kingdom ............... 50675/71

[51] Int. Cl.$^2$ .............................................. A61K 35/00
[52] U.S. Cl. .................................................... 424/114
[58] Field of Search ................................. 424/114, 271

[56] References Cited

U.S. PATENT DOCUMENTS

| | | |
|---|---|---|
| 3,755,588 | 8/1973 | Lund ..................... 424/271 |
| 3,957,764 | 5/1976 | Lund ..................... 424/271 |
| 4,089,963 | 5/1978 | Bamberg et al. ........... 424/271 |

FOREIGN PATENT DOCUMENTS 1241844 8/1971 United Kingdom ..................... 424/271

Primary Examiner—Jerome D. Goldberg
Attorney, Agent, or Firm—Brumbaugh, Graves, Donohue & Raymond

[57] ABSTRACT

An antibacterial synergistic composition consisting essentially of a mixture of a penicillin or cephalosporin derivative of the formula

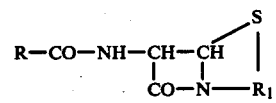

and a penicillin of the formula

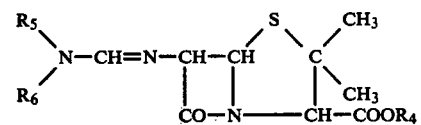

preferably in association with a pharmaceutical carrier.

8 Claims, No Drawings

PENICILLIN COMPOSITION

This application is a continuation-in-part of copending U.S. Application Ser. No. 464,157/74 filed Apr. 25, 1974, which in turn is a continuation-in-part of Ser. No. 302,423 filed Oct. 31, 1972, now abandoned.

This invention relates to new antibacterial synergistic compositions containing penicillin derivatives or cephalosporin derivatives, methods for the preparation of such compositions and a method for the treatment of infectious diseases.

In particular, this invention relates to an antibacterial synergistic composition consisting essentially of a mixture of:

(a) a known, clinically useful penicillin or cephalosporin of the formula

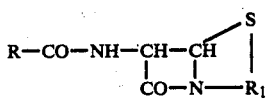

wherein R is a residue of an organic acid, and wherein $R^1$ is selected from the group consisting of the bivalent radicals

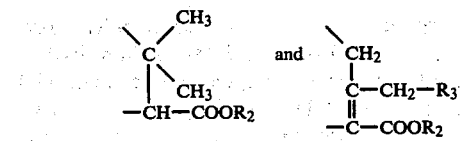

wherein $R_2$ is hydrogen, a pharmaceutically acceptable cation or an in vivo rapidly hydrolyzed pharmaceutically acceptable ester group, and wherein $R_3$ is selected from the group consisting of

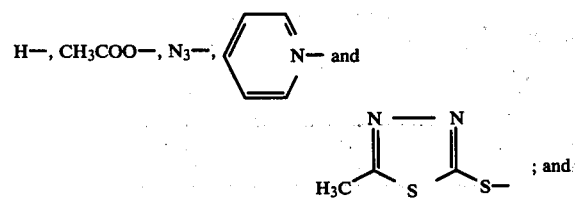

(b) a known, clinically useful penicillin of the formula

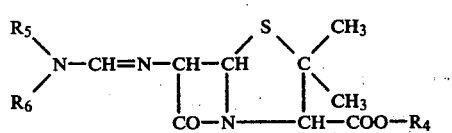

wherein $R_4$ is hydrogen, a pharmaceutically acceptable cation or an in vivo rapidly hydrolyzed pharmaceutically acceptable ester group, and wherein $R_5$ and $R_6$ are lower alkyl groups containing not more than four carbon atoms, or $R_5$ and $R_6$, when taken together with the adjacent nitrogen atom, represent a ring system of the formula

The above described composition contains the compounds of formula I and II in a weight ratio ranging from 10:1 to 1:10, preferably ranging from 2:1 to 1:2. Optionally, the composition can be incorporated in a pharmaceutically acceptable carrier.

It has surprisingly been found that by combining a compound with the general formula I with a compound of the general formula II to form the above described composition, the antibacterial activity of both compounds may be greatly enhanced.

A further useful property is that bacterial organisms may develop resistance to a combination of compounds of the formula I and II less readily than to either of the compounds alone.

A great number of penicillins and cephalosporins of the general formula I are known to have strong antibacterial activity, and such penicillins and cephalosporins have been extensively used for the treatment of infectious diseases caused by Gram-positive and Gram-negative bacteria.

Examples of penicillins and cephalosporins of the formula I are, as disclosed in our grandparent U.S. Application Ser. No. 302,423, the clinically used penicillins and cephalosporins e.g. benzyl-penicillin, phenoxymethylpenicillin, phenoxyethylpenicillin, phenoxypropylpenicillin, 2,6-methoxyphenylpenicillin, 3-phenyl-5-methyl-4-isoxazolylpenicillin, 3-o-chlorophenyl-5-methyl-4-isoxazolylpenicillin, 3-(2,6-dichlorophenyl)-5-methyl-4-isoxazolylpenicillin, 3-(2-fluoro-6-chlorophenyl)-5-methyl-4-isoxazolylpenicillin, 6-(2-ethoxy-1-napthamido)-penicillanic acid, α-carboxybenzylpenicillin, 6-(D-α-aminophenylacetamido)-penicillanic acid, 6-(D-α-amino-p-hydroxyphenylacetamido)-penicillanic acid, α-carboxy-3-thienylmethylpenicillin, 6-(D-α-sulphoaminophenylacetamido)-penicillanic acid, α-hydroxysulphonylbenzylpenicillin, α-indanyloxycarbonyl-benzylpenicillin and further 6-(D-α-amino-3-thienylacetamido)-penicillanic acid, 6-(D-α-azidophenylacetamido)-penicillanic acid, and 6-(D-α-azido-m-fluorophenylacetamido)-penicillanic acid, 2-thienyl-cephalosporin, benzyl-cephalosporin, cyanomethyl-cephalosporin, 4-pyridylthiomethylcephalosporin, 7-(D-α-aminophenylacetamido)-cephalosporanic acid, 7-(D-α-amino-phenylacetamido)desacetoxycephalosporanic acid, 7-(2-thienyl)acetamido-3-(1-pyridylmethyl)-3-cephem-4-carboxylate betaine, 7-(1H-tetrazol-1-yl)acetamido-3-(2-methyl-1,3,4-thiadiazol-5-ylthio)-methyl-3-cephem-4-carboxylic acid, and pharmaceutically acceptable salts thereof formed with pharmaceutically acceptable organic or inorganic bases.

One particularly preferred penicillin of the formula I is the above-mentioned compound 6-(D-α-amino-p-hydroxyphenylacetamido)penicillanic acid, and pharmaceutically acceptable salts thereof.

Penicillins of the general formula II also exhibit strong antibacterial activity, particularly against Gram-negative organisms. These until recently unknown penicillins have been described in Dutch Pat. application No. 7,016,435 and in British Pat. No. 1,293,590.

Examples of compounds of the formula II are 6-[(hexahydro-1H-azepin-1-yl)methyleneamino]-penicillanic acid, 6-[(piperidyl-1-)methyleneamino]-penicillanic acid, 6-[(hexahydro-1(2H)-azocinnyl)methyleneamino]-penicillanic acid, and 6-[(N-ethyl-N-isopropylamino)-methyleneamino]-penicillanic acid.

In the composition of the invention the preferred penicillins of the formula II are those wherein the groups $R_5$ and $R_6$, when taken together with the adjacent nitrogen atom, represent a ring system of the formula

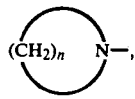

wherein n is 5, 6 or 7.

Preferably n is 6, which means that the preferred compound of the formula II is 6-[(hexahydro-1H-azepin-1-yl)methyleneamino]-penicillanic acid (approved generic name: Mecillinam).

When the composition of the invention is orally administered, the penicillin of the formula II may be in the form of a known ester thereof, which is rapidly hydrolyzed in vivo. Examples of suitable penicillin esters included in the formula II are those wherein the group $R_4$ is an acyloxy-alkyl group, e.g. the acetoxy-methyl, the pivaloyloxy-methyl or the 1″-acetoxy-ethyl group; or an alkyloxycarbonyloxy-alkyl group e.g. the ethoxycarbonyloxymethyl or the 1′-ethoxycarbonyloxyethyl group.

The above mentioned suitable ester groups can be described by the formula

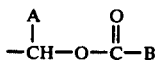

wherein A is hydrogen or methyl, and B is alkyl or alkoxy. Preferably the group B should not contain more than four carbon atoms. The preferred meanings of the group B is ethoxy and tert.butyl.

Penicillin esters of this type, and included in the formula II, are known e.g. from Dutch Pat. application Nos. 7,016,435 and 7,303,434.

Examples of preferred penicillin esters of the formula II are pivaloyloxymethyl 6-[(hexahydro-1H-azepin-1-yl)methyleneamino]penicillanate, acetoxy-methyl 6-[(hexahydro-1H-azepin-1-yl)methyleneamino]penicillanate, pivaloyloxymethyl 6-[(hexahydro-1(2H)-azocinnyl)methyleneamino]penicillanate, ethoxycarbonyloxymethyl 6-[(hexahydro-1H-azepin-1-yl)methyleneamino]-penicillanate, 1′-ethoxycarbonyloxyethyl 6-[(piperidyl-1-)methyleneamino]-penicillanate, 1′-acetoxyethyl 6-[(hexahydro-1H-azepin-1-yl)methyleneamino]penicillanate, 1′-ethoxycarbonyloxyethyl 6-[(hexahydro-1(2H)-azocinnyl)methyleneamino]penicillanate, and 1′-ethoxycarbonyloxyethyl 6-[(hexahydro-1H-azepin-1-yl)methyleneamino]-penicillanate, and pharmaceutically acceptable salts thereof. Two particularly preferred esters of the formula II are pivaloyloxymethyl 6-[(hexahydro-1H-azepin-1-yl)methyleneamino]-penicillanate and 1′-ethoxycarbonyloxy-ethyl 6-[(hexahydro-1H-azepin-1-yl-)methyleneamino]penicillanate.

The composition according to the invention can be prepared by various mixing operations well known for the preparation of compositions containing penicillin or cephalosporins.

The composition of the present invention may be administered either orally or by injection. The composition may have optionally incorporated therewith other substances, e.g. pharmaceutically acceptable solid or liquid carriers or diluents and may be in any of the conventional pharmaceutical forms known to the art for penicillin therapy, for example compositions suitable for oral administration, for example tablets, granules, capsules, dispersible powders for the preparation of aqueous dispersions for oral use, solutions, suspensions or emulsions, or compositions suitable for parenteral administration, for example aqueous or nonaqueous solutions or suspensions, or dispersible powders for the preparation of sterile aqueous dispersions, or compositions suitable for topical administration, for example ointments.

The compositions according to the invention show low toxicity and are well tolerated. In the treatment of bacterial infections in man, the composition of the invention is for example administered in amounts corresponding to 5 to 200 mg/kg/day, of the active ingredients of the composition, preferably in the range of 10 to 100 mg/kg/day in divided dosages, e.g. two, three or four times a day. They are e.g. administered in dosage units containing e.g. 175, 350, 500 and 1000 mg of the active ingredients of the composition.

The following example illustrate the remarkable antibacterial synergistical effect of the compositions according to the invention.

EXAMPLE 1

In vitro-effect of the combination of 6-(D-α-amino-p-hydroxyphenylacetamido)penicillanic acid and 6-[(hexahydro-1H-azepin-1-yl)methyleneamino]penicillanic acid The in vitro activity of 6-(D-α-amino-p-hydroxyphenylacetamido)penicillanic acid (I), 6-[(hexahydro-1H-azepin-1-yl)methyleneamino]penicillanic acid (II) and of a combination (III) of equal parts of the two compounds against clinically isolated enterobacteria was determined in a serial dilution test. Tryptose phosphate broth, containing the appropriate concentrations of the compounds or of the combination of them, was inoculated with $0.5 \times 10^4 - 5 \times 10^4$ organisms of the various microorganisms tested and incubated overnight at 37° C. Minimum inhibitory concentrations (M.I.C.) were taken as the concentrations of the compounds or of the combination at which no visible growth occurred.

| Microorganism | Strain No. | M.I.C. (μg/ml) | | |
|---|---|---|---|---|
| | | I | II | III |
| Escherichia coli | 1/71 | 250 | 31.2 | 1.0 |
| | 7/71 | 31.2 | 31.2 | 2.0 |
| | 17/71 | 62.5 | 15.6 | 3.9 |
| Coliform | 19 | 100 | 25 | 0.78 |
| | 51 | 3.12 | 0.39 | 0.09 |
| Proteus | 20/75 | 0.78 | 100 | 0.18 |
| | 27/75 | >100 | >100 | 0.78 |
| | 34/75 | 0.78 | 50 | 0.09 |
| Klebsiella | 26/75 | 50 | 50 | 0.39 |
| Enterobacter | 18 | >250 | 62.5 | 3.9 |

We claim:

1. An antibacterial synergistic composition comprising a mixture of
   (a) the penicillin 6-(D-α-amino-p-hydroxyphenylacetamido)penicillanic acid or its pharmaceutically acceptable salts (A); and
   (b) a penicillin of the formula

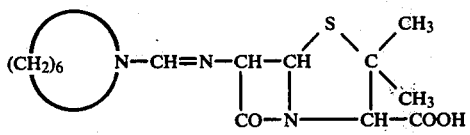

or pharmaceutically acceptable salts or pharmaceutically acceptable in vivo rapidly hydrolyzed esters thereof (C); said composition containing the compounds of formulas A and C in a weight ratio ranging from 10:1 to 1:10.

2. A composition according to claim 1, wherein the compound of the formula II is 6-[(hexahydro-1H-azepin-1-yl)methyleneamino]-penicillanic acid.

3. A composition according to claim 1, wherein the compound of the formula II is pivaloyloxymethyl 6-[(hexahydro-1H-azepin-1-yl)methyleneamino]penicillanate.

4. A composition according to claim 1, wherein the compound of the formula II is 1'-ethoxycarbonyloxyethyl 6-[(hexahydro-1H-azepin-1-yl)methyleneamino]-penicillanate.

5. A composition according to claim 1 in which the weight proportions of the compounds of formulas A and C range from 2:1 to 1:2.

6. An antibacterial synergistic composition comprising a therapeutically effective amount of a mixture of 6-(D-α-amino-p-hydroxyphenylacetamido)penicillanic acid and 6-[(hexahydro-1H-azepin-1-yl)methyleneamino]penicillanic acid, said composition containing said compounds in a weight ratio ranging from 10:1 to 1:10.

7. A composition according to claims 1 or 6 in association with a pharmaceutically acceptable carrier.

8. An antibacterial composition comprising a mixture of
(a) the penicillin (6-D-α-amino-p-hydroxyphenylacetamido)penicillanic acid or its pharmaceutically acceptable salts (A); and
(b) a penicillin of the formula

| Microorganism | Strain No. | M.I.C. (μg/ml) | | |
|---|---|---|---|---|
| | | I | II | III |
| Escherichia coli | 1/71 | 250 | 31.2 | 1.0 |
| | 7/71 | 31.2 | 31.2 | 2.0 |
| | 17/71 | 62.5 | 15.6 | 3.9 |
| Coliform | 19 | 100 | 25 | 0.78 |
| | 51 | 3.12 | 0.39 | 0.09 |
| Proteus | 20/75 | 0.78 | 100 | 0.18 |
| | 27/75 | >100 | >100 | 0.78 |
| | 34/75 | 0.78 | 50 | 0.09 |
| Klebsiella | 26/75 | 50 | 50 | 0.39 |
| Enterobacter | 18 | >250 | 62.5 | 3.9 | or pharmaceutically acceptable salts or pharmaceutically acceptable in vivo hydrolyzed esters thereof (C) selected from the group consisting of acyloxy-alkyl esters and alkyloxycarbonyloxyalkyl esters; said composition containing the compounds of formulas A and C in a weight ratio ranging from 10:1 to 1:10.

* * * * *

UNITED STATES PATENT AND TRADEMARK OFFICE
CERTIFICATE OF CORRECTION

PATENT NO. : 4,203,972
DATED : May 20, 1980
INVENTOR(S) : Bamberg et al.

It is certified that error appears in the above—identified patent and that said Letters Patent is hereby corrected as shown below:

Col. 5, line 28, delete "a therapeutically effective amount of";

Col. 6, line 3, before "composition" insert --synergistic--;

Col. 6, lines 10-24, delete table and insert

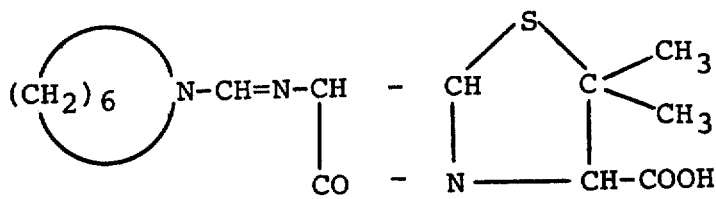

Signed and Sealed this

Sixteenth Day of December 1980

[SEAL]

Attest:

SIDNEY A. DIAMOND

Attesting Officer

Commissioner of Patents and Trademarks